(12) United States Patent
Marsh

(10) Patent No.: US 6,703,330 B1
(45) Date of Patent: Mar. 9, 2004

(54) FLUTED ABSORBENT COMPOSITE

(75) Inventor: David G. Marsh, Federal Way, WA (US)

(73) Assignee: Weyerhaeuser Company, Federal Way, WA (US)

( * ) Notice: Subject to any disclaimer, the term of this patent is extended or adjusted under 35 U.S.C. 154(b) by 236 days.

(21) Appl. No.: 09/667,858

(22) Filed: Sep. 20, 2000

Related U.S. Application Data
(60) Provisional application No. 60/155,459, filed on Sep. 21, 1999.

(51) Int. Cl.[7] .......................... B32B 3/12; B32B 15/08; B32B 27/38; B32B 17/00; A61F 13/15; A61F 13/20
(52) U.S. Cl. .................. 442/381; 442/414; 442/415; 442/416; 442/417; 442/118; 604/368; 604/376; 604/387
(58) Field of Search ................ 442/414–417, 442/118; 604/368, 376, 387

(56) References Cited

U.S. PATENT DOCUMENTS

| | | |
|---|---|---|
| 3,716,449 A | 2/1973 | Gatward et al. |
| 3,868,287 A | 2/1975 | Lewyckyj |
| 3,871,952 A | 3/1975 | Robertson |
| 3,897,784 A | 8/1975 | Fitzgerald |
| 3,938,782 A | 2/1976 | Robertson |
| 4,354,901 A | 10/1982 | Kopolow |
| 4,364,992 A | 12/1982 | Ito et al. |
| 4,443,297 A | 4/1984 | Cheshire et al. |
| 4,551,142 A | 11/1985 | Kopolow |
| 4,559,050 A | 12/1985 | Iskra |
| 4,568,341 A | 2/1986 | Mitchell et al. |
| 4,605,401 A | 8/1986 | Chmelir et al. |
| 4,685,914 A | 8/1987 | Holtman |
| 4,704,116 A | 11/1987 | Enloe |

(List continued on next page.)

FOREIGN PATENT DOCUMENTS

| | | |
|---|---|---|
| EP | 0 339 461 B1 | 2/1989 |
| EP | 0 528 248 | 2/1993 |

(List continued on next page.)

*Primary Examiner*—Terrel Morris
*Assistant Examiner*—Lynda Salvatore
(74) *Attorney, Agent, or Firm*—Christensen O'Connor Johnson Kindness PLLC

(57) ABSTRACT

A fibrous absorbent composite containing absorbent material, methods for its formation, and absorbent articles that include the composite are described. The composite is a fibrous structure that includes absorbent material dispersed throughout the composite and in increased concentration in bands that extend along the composite's length.

17 Claims, 4 Drawing Sheets

U.S. PATENT DOCUMENTS

| | | | |
|---|---|---|---|
| 4,798,603 A | 1/1989 | Meyer et al. | |
| 4,885,204 A | 12/1989 | Bither et al. | |
| 4,988,344 A | 1/1991 | Reising et al. | |
| 4,988,345 A | 1/1991 | Reising | |
| 5,061,259 A | 10/1991 | Goldman et al. | |
| 5,102,597 A | 4/1992 | Roe et al. | |
| 5,134,007 A | 7/1992 | Reising et al. | |
| 5,137,537 A | 8/1992 | Herron et al. | |
| 5,147,343 A | 9/1992 | Kellenberger | |
| 5,147,345 A | 9/1992 | Young et al. | |
| 5,149,335 A | 9/1992 | Kellenberger et al. | |
| 5,176,669 A * | 1/1993 | Klemp | 604/387 |
| 5,215,627 A | 6/1993 | Willis et al. | |
| 5,217,445 A | 6/1993 | Young et al. | |
| 5,277,915 A | 1/1994 | Provonchee et al. | |
| 5,281,207 A | 1/1994 | Chmielewski et al. | |
| 5,284,610 A | 2/1994 | Tai | |
| 5,324,561 A | 6/1994 | Rezai et al. | |
| 5,330,822 A | 7/1994 | Berg et al. | |
| 5,350,370 A | 9/1994 | Jackson et al. | |
| 5,354,290 A | 10/1994 | Gross | |
| 5,360,420 A | 11/1994 | Cook et al. | |
| 5,364,382 A | 11/1994 | Latimer et al. | |
| 5,372,877 A | 12/1994 | Kannenkeril | |
| 5,415,643 A | 5/1995 | Kolb | |
| 5,422,169 A | 6/1995 | Roe | |
| 5,425,725 A | 6/1995 | Tanzer et al. | |
| 5,429,629 A | 7/1995 | Latimer et al. | |
| 5,486,167 A | 1/1996 | Dragoo et al. | |
| 5,505,718 A | 4/1996 | Roe et al. | |
| 5,509,915 A | 4/1996 | Hanson et al. | |
| 5,522,810 A | 6/1996 | Allen, Jr. et al. | |
| H1565 H | 7/1996 | Brodof et al. | |
| 5,531,728 A | 7/1996 | Lash | |
| 5,562,646 A | 10/1996 | Goldman et al. | |
| 5,593,399 A * | 1/1997 | Tanzer et al. | 604/368 |
| 5,597,873 A | 1/1997 | Chambers et al. | |
| 5,599,335 A | 2/1997 | Goldman et al. | |
| 5,601,542 A | 2/1997 | Melius et al. | |
| 5,607,550 A | 3/1997 | Akers | |
| 5,637,105 A | 6/1997 | Tanaka et al. | |
| 5,651,862 A | 7/1997 | Anderson et al. | |
| 5,653,702 A | 8/1997 | Brohammer et al. | |
| 5,669,894 A | 9/1997 | Goldman et al. | |
| 5,698,078 A | 12/1997 | Mizukami et al. | |
| 5,733,273 A | 3/1998 | Ahr | |
| 5,736,219 A | 4/1998 | Suehr et al. | |
| 5,741,400 A | 4/1998 | Kwak | |
| 5,749,863 A * | 5/1998 | Payne | 604/376 |
| 5,788,684 A | 8/1998 | Abuto et al. | |
| 5,792,129 A | 8/1998 | Johansson et al. | |
| 5,792,513 A | 8/1998 | Koslow et al. | |
| 5,795,439 A | 8/1998 | Euripides et al. | |
| 5,821,179 A | 10/1998 | Masaki et al. | |
| 5,830,202 A | 11/1998 | Bogdanski et al. | |
| 5,836,929 A | 11/1998 | Bewick-Sonntag et al. | |
| 5,843,059 A | 12/1998 | Niemeyer et al. | |
| 5,843,063 A | 12/1998 | Anderson et al. | |
| 5,843,575 A | 12/1998 | Wang et al. | |
| 5,843,852 A | 12/1998 | Dutkiewicz et al. | |
| 5,849,000 A | 12/1998 | Anjur et al. | |
| 5,849,405 A | 12/1998 | Wang et al. | |
| 5,851,672 A | 12/1998 | Wang et al. | |
| 5,853,867 A | 12/1998 | Harada et al. | |
| 5,855,572 A | 1/1999 | Schmidt | |
| 5,858,535 A | 1/1999 | Wang et al. | |
| 5,868,724 A | 2/1999 | Dierckes, Jr. et al. | |
| 5,873,867 A | 2/1999 | Coles et al. | |
| 5,891,120 A | 4/1999 | Chmielewski | |
| 5,895,379 A | 4/1999 | Litchholt et al. | |
| 5,925,439 A | 7/1999 | Haubach | |
| 5,941,862 A | 8/1999 | Haynes et al. | |
| 5,941,863 A | 8/1999 | Guidotti et al. | |
| 5,972,487 A | 10/1999 | Duenk et al. | |
| 5,977,014 A | 11/1999 | Plischke et al. | |
| 6,015,608 A | 1/2000 | Koslow | |
| 6,080,909 A | 6/2000 | Österdahl et al. | |
| 6,086,950 A | 7/2000 | Masaki et al. | |
| 6,129,717 A | 10/2000 | Fujioka et al. | |
| 6,177,605 B1 | 1/2001 | Trombetta et al. | |
| 2001/0053904 A1 * | 12/2001 | Abuto | 604/385.101 |

FOREIGN PATENT DOCUMENTS

| | | |
|---|---|---|
| EP | 0 437 816 B1 | 7/1995 |
| EP | 0 685 212 | 12/1995 |
| EP | 0 719 531 A1 | 3/1996 |
| EP | 0 724 870 A2 | 7/1996 |
| EP | 0 528 248 B1 | 10/1996 |
| EP | 748 894 A2 | 12/1996 |
| EP | 0217666 A2 | 4/1997 |
| FR | 2468689 | 8/1981 |
| GB | 2 060 018 A | 4/1981 |
| GB | 2 120 696 A | 7/1983 |
| GB | 2 254 255 A | 7/1992 |
| GB | 2284831 A | 6/1995 |
| GB | 2 301 362 A | 4/1996 |
| JP | 09 156012 | 6/1997 |
| JP | 09156013 | 6/1997 |
| WO | WO 93/06804 | 4/1993 |
| WO | WO 95 13778 | 5/1995 |
| WO | WO 97/05839 | 2/1997 |
| WO | WO 97/18783 | 5/1997 |
| WO | WO 97/21453 | 6/1997 |
| WO | WO 98/24392 | 6/1998 |
| WO | WO 98/37846 | 9/1998 |
| WO | WO 98/47455 | 10/1998 |
| WO | WO 99/32721 | 7/1999 |
| WO | WO 00/41882 | 7/2000 |
| WO | WO 00/47153 | 8/2000 |

\* cited by examiner

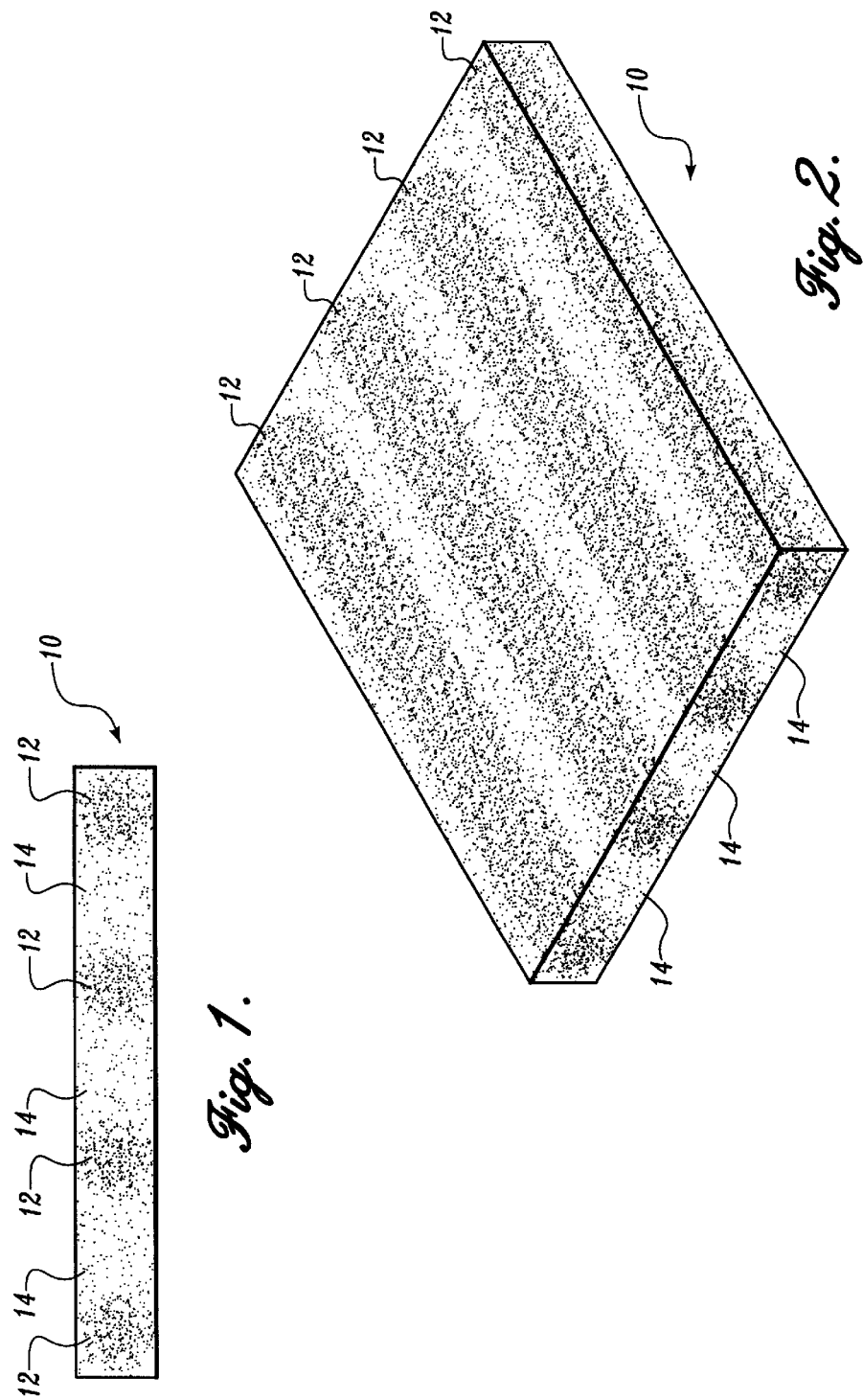

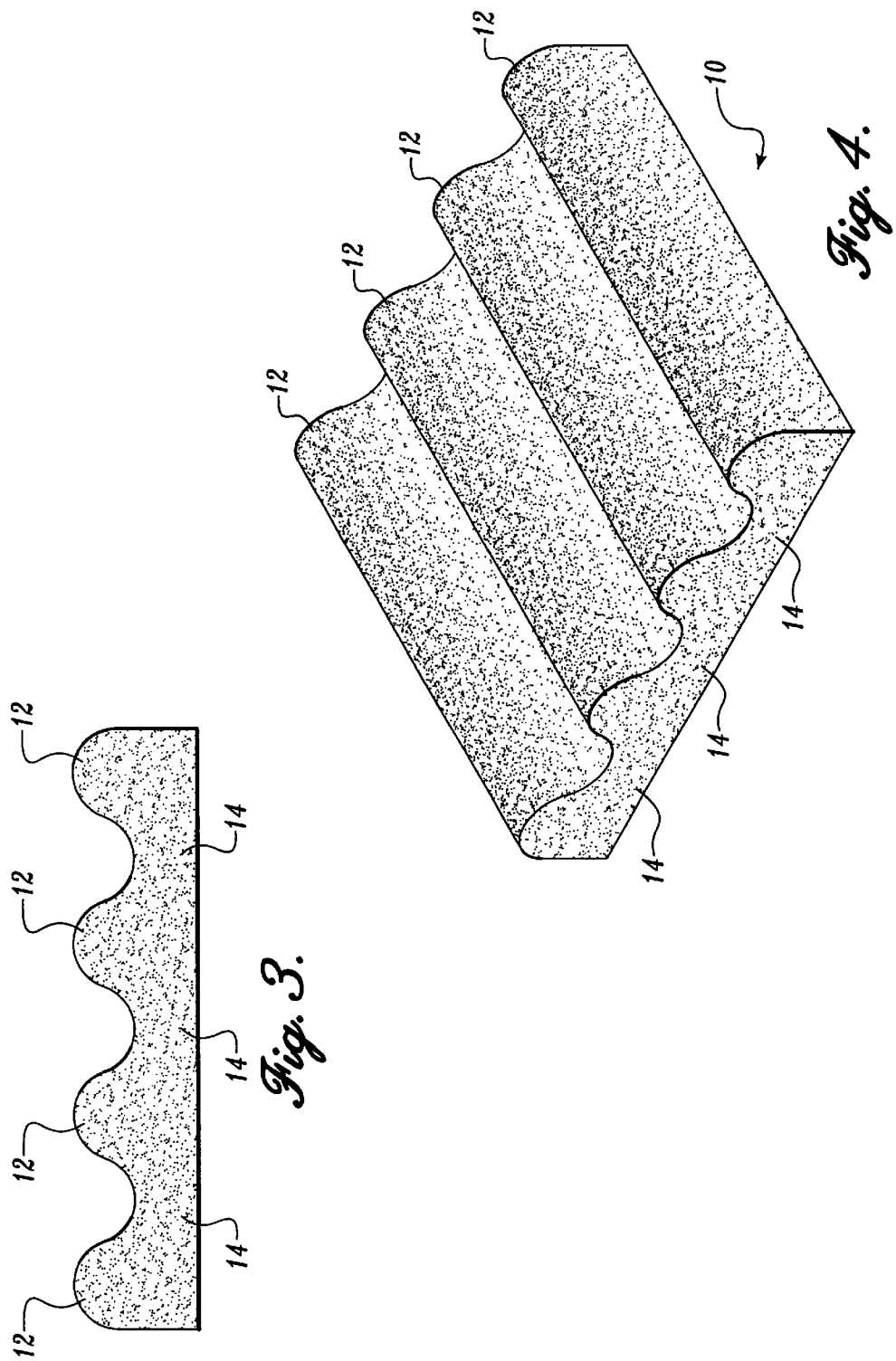

FLUTED ABSORBENT COMPOSITE

CROSS-REFERENTE TO RELATED APPLICATION

This application is a continuation of U.S. provisional application No. 60/155,459, filed Sep. 21, 1999, the benefit of the priority of the filing date of which is hereby claimed under 35 U.S.C. §119.

FIELD OF THE INVENTION

The present invention relates generally to an absorbent composite and, more particularly, to an air-laid composite that includes absorbent material.

BACKGROUND OF THE INVENTION

Cellulose fibers derived from wood pulp are used in a variety of absorbent articles, for example, diapers, incontinence products, and feminine hygiene products. It is desirable for the absorbent articles to have a high absorbent capacity for liquid, rapid liquid acquisition, low rewet, as well as to have good dry and wet strength characteristics for durability in use and effective fluid management. The absorbent capacity of articles made from cellulose fibers is often enhanced by the addition of absorbent materials, such as superabsorbent polymers. Superabsorbent polymers known in the art have the capability to absorb liquids in quantities from 5 to 100 times or more their weight. Thus, the presence of superabsorbent polymers greatly increases the liquid holding capacity of absorbent articles made from cellulose.

However, absorbent composites that contain superabsorbent materials commonly suffer from gel blocking. Upon liquid absorption, superabsorbent materials tend to coalesce and form a gelatinous mass which prevents the wicking of liquid to unwetted portions of the composite. By preventing distribution of acquired liquid from a composite's unwetted portions, gel blocking precludes the effective and efficient use of superabsorbent materials in fibrous composites. The wicking capacity of conventional fibrous composites that include relatively homogeneous distributions of superabsorbent material is generally significantly reduced after initial liquid insult. The diminished capacity of such fibrous composites results from narrowing of capillary acquisition and distribution channels that accompanies superabsorbent material swelling. The diminution of absorbent capacity and concomitant loss of capillary distribution channels for conventional absorbent cores that include superabsorbent material is manifested by decreased liquid acquisition rates and far from ideal liquid distribution on successive liquid insults.

Accordingly, there exists a need for an absorbent composite that includes superabsorbent material and that effectively acquires and wicks liquid throughout the composite and distributes the acquired liquid to absorbent material where the liquid is efficiently absorbed and retained without gel blocking. A need also exists for an absorbent composite that continues to acquire and distribute liquid throughout the composite on successive liquid insults. In addition, there exists a need for an absorbent composition containing superabsorbent materials that exhibits the advantages associated with wet-laid composites including wet strength, absorbent capacity and acquisition, liquid distribution, softness, and resilience. The present invention seeks to fulfill these needs and provides further related advantages.

SUMMARY OF THE INVENTION

In one aspect, the present invention provides a fibrous absorbent composite that includes absorbent material distributed throughout the composite and in selected regions of the composite. The concentration of absorbent material in these regions can be varied to provide a composite having variable absorbent material concentration. In one embodiment, the composite includes absorbent material dispersed in bands across the composite's width and that extend along the composite's length. On contact with liquid, the composite's bands enriched with absorbent material swell with acquired liquid and expand and rise from the composite's wetted surface to form ridges and to provide a fluted structure. The wetted composite's fluted structure enhances liquid wicking, acquisition, and distribution on subsequent liquid insult.

In another aspect of the invention, a method for forming an absorbent composite having variable absorbent material content is provided. In one embodiment, the method includes increasing the concentration of absorbent material in the composite by adding absorbent material to selective regions of the composite. In another embodiment, the method provides for forming regions of increased absorbent material concentration in the composite by selectively increasing the composite's basis weight. In the method, the composite is formed by selectively densifying a substantially homogeneous composite containing fibers and absorbent material.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a lateral cross-sectional view of a representative fluted absorbent composite formed in accordance with the present invention;

FIG. 2 is a perspective view of the composite shown in FIG. 1;

FIG. 3 is a lateral cross-sectional view of a representative fluted absorbent composite of the present invention in a wetted state;

FIG. 4 is a perspective view of the wetted composite shown in FIG. 3;

DETAILED DESCRIPTION OF THE PREFERRED EMBODIMENT

Figure 5:
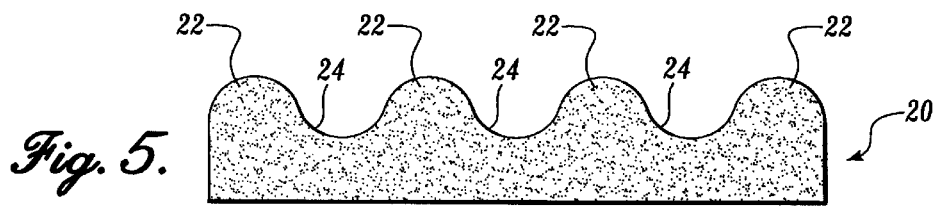
FIG. 5 is a lateral cross-sectional view of a representative composite that includes a relatively homogeneous distribution of fibers and absorbent material.

The absorbent composite of the present invention is a fibrous composite that includes absorbent material distributed throughout the composite and in selected regions of the composite. The concentration of absorbent material in these regions can be varied to provide a composite having variable absorbent material content. In one embodiment, the absorbent composite includes absorbent material dispersed in bands across the composite's width (i.e., cross-machine direction) and that extend along the composite's length (i.e., machine direction). Distribution zones that are composed primarily of fibers lie between the composite's bands enriched with absorbent material. The composite's fibrous distribution zones serve to acquire liquid contacting the composite and to distribute the acquired liquid throughout the composite and, ultimately, to the absorbent material. The absorbent material serves to absorb and retain liquid acquired by the composite.

The absorbent composite can be advantageously incorporated into a variety of absorbent articles such as diapers including disposable diapers and training pants; feminine care products including sanitary napkins, tampons, and pant liners; adult incontinence products; toweling; surgical and dental sponges; bandages; food tray pads; and the like. Because the composite is highly absorbent, the composite can be included into an absorbent article as a liquid storage core. In such a construct, the composite can be combined with one or more other composites or layers including, for example, an acquisition and/or a distribution layer. Because of the composite's capacity to rapidly acquire and distribute liquid, the composite can also serve as an liquid management layer that acquires and releases a portion of the acquired liquid to an underlying storage core. Thus, in another embodiment, the absorbent composite can be combined with a storage core to provide an absorbent construct that is useful in absorbent articles.

The absorbent composite of the present invention is a fluted storage composite. As used herein, the term "fluted" refers to the nature of the composite, which on wetting, develops ridges and becomes a fluted structure as a result of absorbent material expansion. As noted above, the composite includes regions (i.e., bands) enriched with absorbent material that are distributed across the composite's width and that extend in bands along the composite's length. On contact with liquid acquired by the fibrous composite, the absorbent material swells resulting in a wetted composite having ridges that include swollen absorbent material. The composite's ridges are separated by distribution zones or channels, which are fibrous regions of the composite that include lesser amounts of absorbent material relative to the composite's absorbent material enriched regions.

The banded nature of the fluted absorbent composite of the present invention is illustrated in FIGS. 1–4. Referring to FIGS. 1 and 2, a representative fluted absorbent composite indicated generally by reference numeral 10 formed in accordance with the present invention includes regions 12 (i.e., liquid storage zones) enriched with absorbent material and regions 14 (i.e., liquid distribution zones) that are generally fibrous regions and include relatively lesser amounts of absorbent material compared to regions 12.

Liquid is rapidly acquired by the predominantly fibrous regions of the composite when the absorbent composite is contacted with liquid. The fibrous regions are relatively open and porous in nature and promote rapid liquid acquisition, wicking, and distribution. Liquid acquired by the composite generally travels rapidly longitudinally through the fibrous composite along the composite's length via the distribution zones (i.e., regions 14) and is absorbed by regions of the composite enriched with absorbent material (i.e., regions 12). The acquired liquid is generally wicked laterally into the absorbent material as the liquid is distributed along the composite's length.

For the fluted composite, successive liquid insults are absorbed at even greater rate through the establishment of flutes and corresponding channels on initial liquid insult. On wetting, the composite of the present invention becomes on a fluted structure having channels for rapidly acquiring additional liquid and distributing the liquid to sites that are remote to insult. For the fluted composite, acquisition times for subsequent liquid insult are generally less than that for the initial acquisition. Reduced acquisition times for successive liquid insults is not generally observed for conventional absorbent constructs. Because conventional absorbent structures cannot form a fluted structure and therefore lack channels for distributing additional liquid, acquisition times for these structures generally increase with successive liquid insults. Increased acquisition time can be attributed to the fact that liquid is only slowly acquired and distributed through a composite's saturated regions to more remote regions of the composite that are capable of absorbing liquid. Thus, the fluted absorbent composite provides initial liquid acquisition rates that are generally comparable to or greater than those for conventional absorbent structures. The composite also has significantly increased rates of liquid acquisition for successive liquid acquisition relative to conventional composites.

Wet structures of the fluted absorbent composite of the present invention are shown in FIGS. 3 and 4. These figures illustrate the fluted nature of the composite, which results from liquid contact and swelling and expansion of absorbent material. Referring to FIGS. 3 and 4, absorbent material enriched regions 12 (i.e., liquid storage regions) are shown as ridges separated by regions 14 (i.e., liquid distribution zones) that form valley floors or channels between the ridges. Due at least in part to the fluted structure of the wetted fibrous composite, subsequent liquid insults are rapidly absorbed by the composite compared to composites that contain absorbent material in other configurations, for example, composites in which absorbent material is distributed substantially uniformly throughout the composite.

Fibers are a principal component of the fluted absorbent composite of this invention. Fibers suitable for use in the present invention are known to those skilled in the art and include any fiber from which an absorbent composite can be formed. Suitable fibers include natural and synthetic fibers. Combinations of fibers including combinations of synthetic and natural fibers, and treated and untreated fibers, can also be suitably used in the composite. In a preferred embodiment, the absorbent composite of the present invention includes cellulosic fibers, hardwood fibers, chemithermomechanical pulp fibers (i.e., CTMP) and, more preferably, crosslinked cellulosic fibers.

Generally, fibers are present in the composite in an amount from about 20 to about 90 weight percent, preferably from about 50 to about 70 weight percent, based on the total weight of the composite. In a preferred embodiment, the composite includes about 60 weight percent fibers.

Cellulosic fibers can be a basic component of the fluted absorbent composite. Although available from other sources, cellulosic fibers are derived primarily from wood pulp. Suitable wood pulp fibers for use with the invention can be obtained from well-known chemical processes such as the Kraft and sulfite processes, with or without subsequent bleaching. Pulp fibers can also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. Softwoods and hardwoods can be used. Details of the selection of wood pulp fibers are well known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

The wood pulp fibers of the present invention can also be pretreated prior to use with the present invention. This pretreatment may include physical treatment, such as subjecting the fibers to steam, or chemical treatment, for example, crosslinking the cellulose fibers using any one of a variety of crosslinking agents. Crosslinking increases fiber bulk and resiliency, and thereby can improve the composite's absorbency. Generally, crosslinked fibers are twisted or crimped. The use of crosslinked fibers allows the composite to be more resilient, softer, bulkier, and to have enhanced wicking. Suitable crosslinked cellulose fibers produced from southern pine are available from Weyerhaeuser Company under the designation NHB416. Crosslinked cellulose fibers and methods for their preparation are disclosed in U.S. Pat. Nos. 5,437,418 and 5,225,047 issued to Graef et al., expressly incorporated herein by reference.

Crosslinked fibers are prepared by treating fibers with a crosslinking agent. Suitable cellulose crosslinking agents include aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chung; U.S. Pat. No. 4,935,022, issued to Lash etal.; U.S. Pat. No. 4,889,595, issued to Herron et al.; U.S. Pat. No. 3,819,470, issued to Shaw et al.; U.S. Pat. No. 3,658,613, issued to Steijer et al.; and U.S. Pat. No. 4,853,086, issued to Graef et al., all of which are expressly incorporated herein by reference in their entirety. Cellulose fibers have also been crosslinked by carboxylic acid crosslinking agents including polycarboxylic acids. U.S. Pat. Nos. 5,137,537; 5,183,707; and 5,190,563, describe the use of $C_2$–$C_9$ polycarboxylic acids that contain at least three carboxyl groups (e.g., citric acid and oxydisuccinic acid) as crosslinking agents.

Suitable urea-based crosslinking agents include methylolated ureas, methylolated cyclic ureas, methylolated lower alkyl cyclic ureas, methylolated dihydroxy cyclic ureas, dihydroxy cyclic ureas, and lower alkyl substituted cyclic ureas. Specific preferred urea-based crosslinking agents include dimethyldihydroxy urea (DMDHU, 1,3-dimethyl-4,5-dihydroxy-2-imidazolidinone), dimethylol dihydroxyethylene urea (DMDHEU, 1,3-dihydroxymethyl-4,5-dihydroxy-2-imidazolidinone), dimethylol urea (DMU, bis[N-hydroxymethyl] urea), dihydroxy-ethylene urea (DHEU, 4,5-dihydroxy-2-imidazolidinone), dimethylolethylene urea (DMEU, 1,3-dihydroxymethyl-2-imidazolidinone), and dimethyldihydroxyethylene urea (DDI, 4,5-dihydroxy-1,3-dimethyl-2-imidazolidinone).

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acids crosslinking agents include polymeric polycarboxylic acids such as poly(acrylic acid), Poly(methacrylic acid), Poly(maleic acid), poly(methylvinylether-co-maleate) copolymer, poly(methyl-vinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents may also be used.

The crosslinking agent can include a catalyst to accelerate the bonding reaction between the crosslinking agent and cellulose fiber. Suitable catalysts include acidic salts, such as ammonium chloride, ammonium sulfate, aluminum chloride, magnesium chloride, and alkali metal salts of phosphorous-containing acids.

Although not to be construed as a limitation, examples of pretreating fibers include the application of surfactants or other liquids which modify the surface chemistry of the fibers. Other pretreatments include incorporation of antimicrobials, pigments, dyes and densification or softening agents. Fibers pretreated with other chemicals, such as thermoplastic and thermosetting resins also may be used. Combinations of pretreatments also may be employed. Similar treatments can also be applied after the composite formation in post-treatment processes.

Cellulosic fibers treated with particle binders and/or densification/softness aids known in the art can also be employed in accordance with the present invention. The particle binders serve to attach other materials, such as cellulosic fiber superabsorbent polymers, as well as others, to the cellulosic fibers. Cellulosic fibers treated with suitable particle binders and/or densification/softness aids and the process for combining them with cellulose fibers are disclosed in the following U.S. patents and patent applications: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Patent No. 5,300,192, entitled "Wet-laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Patent No. 5,308,896, entitled "Particle Binders for High-Bulk Fibers"; (6) Ser. No. 07/931,279, filed Aug. 17, 1992, entitled "Particle Binders that Enhance Fiber Densification"; (7) Ser. No. 08/107,469, filed Aug. 17, 1993, entitled "Particle Binders"; (8) Ser. No. 08/107,219, filed Aug. 17, 1993, entitled "Particle Binding to Fibers"; (9) Ser. No. 08/107,467, filed Aug. 17, 1993, entitled "Binders for Binding Water Soluble Particles to Fibers"; (10) U.S. Pat. No. 5,547,745, entitled "Particle Binders"; (11) Ser. No. 08/108,218, filed Aug. 17, 1993, entitled "Particle Binding to Fibers" and (12), U.S. Pat. No. 5,308,896, entitled "Particle Binders for High-Bulk Fibers"; all expressly incorporated herein by reference.

In addition to natural fibers, synthetic fibers including polymeric fibers, such as polyolefin, polyamide, polyester, polyvinyl alcohol, and polyvinyl acetate fibers can also be used in the absorbent composite of the present invention. Suitable polyolefin fibers include polyethylene and polypropylene fibers. Suitable polyester fibers include polyethylene terephthalate fibers. Other suitable synthetic fibers include, for example, nylon and rayon fibers. The absorbent composite can also include combinations of natural and synthetic fibers.

In one preferred embodiment, the absorbent composite includes a combination of pulp fibers (e.g., Weyerhaeuser designation NB416) and crosslinked cellulosic fibers (e.g., Weyerhaeuser designation NBH416). Pulp fibers preferably present in such a combination in an amount from about 15 to about 85 weight percent. In another preferred embodiment, the absorbent composite includes a combination of pulp fibers present in the composite in about 50 weight percent and crosslinked cellulosic fibers present in the composite in about 50 weight percent based on the total weight of fibers.

The fluted absorbent composite of the present invention can serve as a storage layer for acquired liquids when incorporated into an absorbent article. To effectively retain acquired liquids, the composite includes absorbent material.

As described above, absorbent material is generally located throughout the composite and in increased concentrations in selected regions of the composite. These selected regions include bands incorporated into the composite. The bands are positioned across the composite's width and extend along the composite's length. The composite's bands are regions of the composite that are enriched with absorbent material. The bands of absorbent material can be configured in virtually any shape, size, and composite location. Suitable configurations of the composite's bands include any configuration that does not significantly impede liquid acquisition or promote gel blocking. The composite's distribution zones also include some absorbent material. However, the liquid absorbent capacity of the absorbent material in the composite's bands is significantly greater than the absorbent material present in the composite's distribution zones.

As use herein, the term "absorbent material" refers to a material that absorbs water and that generally has an absorbent capacity greater than the cellulosic fibrous component of the composite. Preferably, the absorbent material is a water swellable, generally water insoluble material capable of absorbing at least about 5, desirably about 20, and preferably about 100 times or more its weight in water. The absorbent material can be swellable in the dispersion medium utilized in the composite forming method. In a preferred embodiment, the absorbent material is untreated and swellable in the dispersion medium.

The amount of absorbent material present in the composite can vary greatly depending on the composite's intended use. The amount of absorbent material present in a composite incorporated into as an absorbent core for an infant's diaper can be from about 10 to about 80 weight percent, preferably from about 30 to about 50 weight percent, based on the total weight of the composite.

The absorbent material may include natural materials such as agar, pectin, and guar gum, and synthetic materials, such as synthetic hydrogel polymers. Synthetic hydrogel polymers include, for example, carboxymethyl cellulose, alkaline metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulphonic acid, polyacrylates, polyacrylamides, and polyvinyl pyridine among others. In a preferred embodiment, the absorbent material is a superabsorbent material. As used herein, a "superabsorbent material" refers to a polymeric material that is capable of absorbing large quantities of fluid by swelling and forming a hydrated gel (i.e., a hydrogel). In addition to absorbing large quantities of fluids, superabsorbent polymers can also retain significant amounts of bodily fluids under moderate pressure.

Superabsorbent materials generally fall into three classes: starch graft copolymers, crosslinked carboxymethylcellulose derivatives, and modified hydrophilic polyacrylates. Examples of such absorbent polymers include hydrolyzed starch-acrylonitrile graft copolymers, neutralized starch-acrylic acid graft copolymers, saponified acrylic acid ester-vinyl acetate copolymers, hydrolyzed acrylonitrile copolymers or acrylamide copolymers, modified crosslinked polyvinyl alcohol, neutralized self-crosslinking polyacrylic acids, crosslinked polyacrylate salts, carboxylated cellulose, and neutralized crosslinked isobutylene-maleic anhydride copolymers.

Superabsorbent polymers are available commercially, for example, polyacrylates from Clariant of Portsmouth, Virginia. These superabsorbent polymers come in a variety of sizes, morphologies and absorbent properties (available from Clariant under trade designations such as IM 3500 and IM 3900). Other superabsorbent polymers are marketed under the trademarks SANWET (supplied by Sanyo Kasei Kogyo Kabushiki Kaisha), and SXM77 and SR1001 (supplied by Stockhausen of Greensboro, N.C.). Other superabsorbent materials are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102.340; and U.S. Pat. No. 4,818,598, all expressly incorporated herein by reference. Products such as diapers that incorporate superabsorbent materials are described in U.S. Pat. No. 3,699,103 and U.S. Pat. No. 3,670,731.

Suitable superabsorbent materials useful in the absorbent composite of the present invention include superabsorbent particles and superabsorbent fibers.

The fluted absorbent composite of the present invention can be formed by air-laid methods known to those of ordinary skill in the pulp processing art. Representative air-laid processes are generally described in U.S. Pat. Nos. 4.640,810 and 4,065,832, both expressly incorporated herein by reference. Generally, air-laid fibrous webs that include absorbent materials such as superabsorbent materials are known in the art. In these webs, absorbent materials are conventionally distributed uniformly throughout the web. Conventional air-laid webs that contain absorbent material typically suffer gel blocking which limits the rate of liquid acquisition, distribution, and can adversely impact absorbent capacity. Air-laid webs also tend to have lower acquisition rates, absorbent capacity, and tensile strength compared to wet-laid fibrous webs. Despite these limitations, the air-laid composites formed in accordance with the present invention have enhanced liquid absorbent properties, including increased acquisition rate, compared to air-laid composites having absorbent material uniformly distributed throughout the entire web.

The fluted absorbent composite of the present invention is a composite having absorbent material concentrations that vary between adjacent regions of the composite. The variation in absorbent material concentration provides a composite having differential liquid absorption and swelling characteristics.

The composite can be formed by any method that provides a fibrous composite having variable absorbent material content. For example, the composite can be formed by varying the basis weight of a composite formed from a homogeneous blend of absorbent material and fibers (e.g., a fibrous composite having a relatively uniform concentration of absorbent material). Alternatively, the composite can be formed by selectively varying absorbent material concentration in the composite (i.e., across the composite's width to provide bands or regions that are enriched with absorbent material).

Variable basis weight composites can be formed by a number of methods including methods that affect the laydown of materials (i.e., fibers and absorbent material) during the air-lay process. For example, a composite having variable basis weight can be formed by creating zones of differing porosity or air permeability on the foraminous support (e.g., forming wire) on which the composite is formed. Airflows carrying fibers and absorbent material will bias to lower resistance zones on the support (i.e., material flows bias toward high porosity). In such a method, higher basis weight regions are created in the composite where flow through the support is least restrictive and lower basis weight regions are created where the flow is more restricted.

The support's backing plate can be shaped into patterns that permit drawing forming air through areas of the support at a rate that is greater than for other areas. Such a method also biases the laydown of material to provide a composite having higher basis weight regions (i.e., regions of higher airflow) and lower basis weight regions (i.e., regions of lower airflow).

The methods noted above can also provide fibrous webs having absorbent material concentration gradients. In these methods, a previously deposited fibrous web can be subjected to forming airflow carrying absorbent material. In such a method, absorbent material applied to the deposited web is distributed throughout the web based on airflow through the deposited web.

Alternatively, absorbent material can be added to a fibrous web by any other method that provides for the formation of bands or other absorbent material enriched regions in the composite.

Composites of the present invention having variable basis weight and variable absorbent material concentration can also be formed from composites that are relatively homogeneous blends of fibers and absorbent material (i.e., composites having a relatively uniform concentration of absorbent material). In the method, fibers and absorbent material are first laid on a foraminous support to provide a composite having a homogeneous blend of fibers and absorbent material. Following deposition, the homogeneous air-laid web's upper surface is scarfed (i.e., removed) to provide a web having ridges and valleys. A representative homogeneous web formed by air laying fibers and absorbent material followed by scarfing is shown in FIG. 5. Referring to FIG. 5, scarfed web 20 includes ridges 22 and valleys 24. After'scarfing, the homogeneous composite is then densified to, for example, a relatively uniform thickness (i.e., caliper). On densification, the materials in the scarfed web's ridges are compacted. In a preferred embodiment, densification provides an air-laid web having a relatively uniform in thickness. As a result of densification, the method provides a composite that includes regions having increased basis weight and regions having increased absorbent material concentration. When densification results in a web having a relatively uniform thickness, the method provides a composite that can be represented by composite 10 shown in FIG. 1. Referring again to FIG. 1, composite 10 includes regions 12 that are enriched with absorbent material. In accordance with the method noted above, regions 12 have an absorbent material concentration that is increased relative to regions 14. Furthermore, regions 12 also have a basis weight that is increased relative to regions 14.

Figure 6:
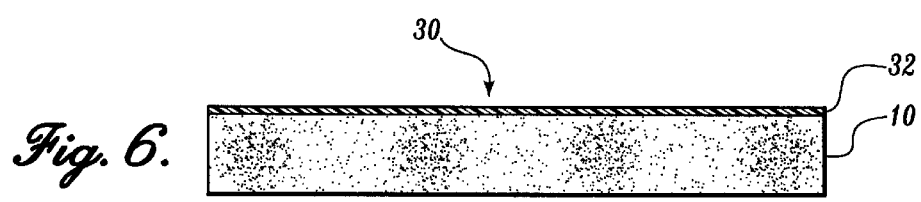
FIG. 6 is a lateral cross-sectional view of an absorbent construct that includes a representative fluted absorbent composite formed in accordance with the present invention.
Figure 7:
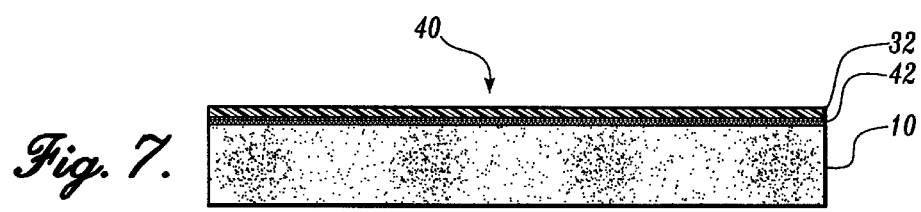
FIG. 7 is a lateral cross-sectional view of another absorbent construct that includes a representative fluted absorbent composite formed in accordance with the present invention.

The fluted absorbent composite of the present invention can be incorporated as an absorbent core or storage layer in an absorbent article including, for example, a diaper or feminine care product. The absorbent composite can be used alone, or as illustrated in FIGS. 6 and 7, can be used in combination with one or more other layers. FIG. 6 illustrates absorbent construct 30 where composite 10 is employed as a storage layer in combination with an upper acquisition layer 32. As illustrated in FIG. 7, construct 40 includes a third layer 42 (e.g., distribution layer) that can also be employed, if desired, with composite 10 and acquisition layer 32.

Figure 8:
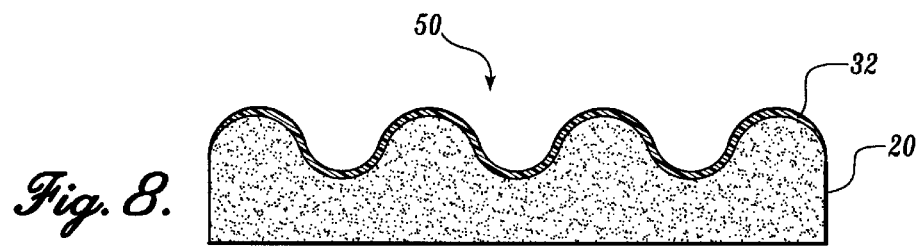
FIG. 8 is a lateral cross-sectional view of the composite shown in FIG. 5 with an overlying acquisition layer.
Figure 9:
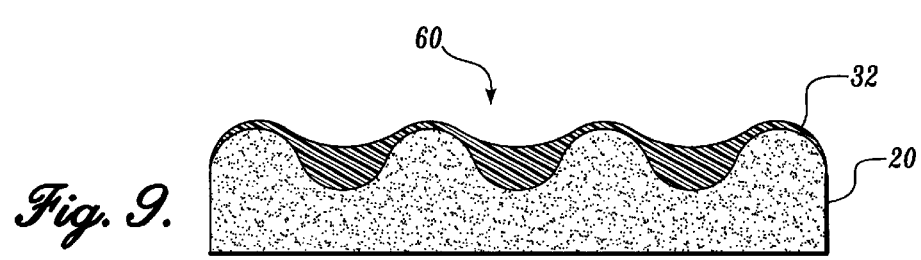
FIG. 9 is a lateral cross-sectional view of the composite shown in FIG. 5 with an overlying acquisition layer.

Alternatively, construct 30 can be formed by overlying an acquisition layer on a scarfed web followed by densification. Referring to FIG. 8, construct 50 includes scarfed web 20 and acquisition layer 32. Depending on the amount of contact desired between the acquisition layer and storage core, the acquisition layer can be formed to substantially occupy the valleys formed in the scarfed web. Referring to FIG. 9, construct 60 includes scarfed web 20 and acquisition layer 32, which substantially occupies the web's valleys. Densification of constructs 50 or 60 provides construct 30.

Figure 10:
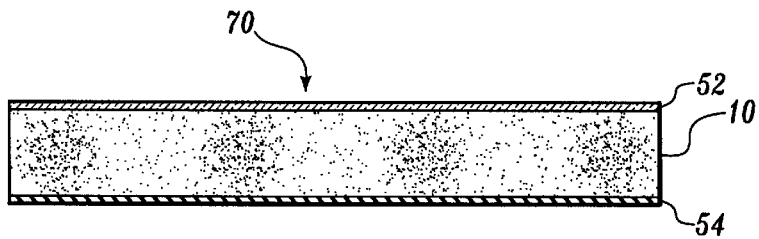
FIG. 10 is a lateral cross-sectional view of a portion of an absorbent article incorporating a representative fluted absorbent composite formed in accordance with the present invention.
Figure 11:
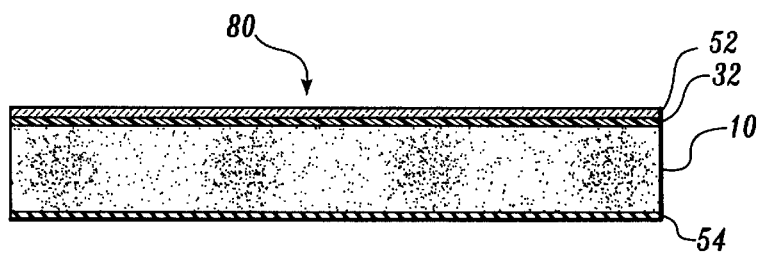
FIG. 11 is a lateral cross-sectional view of a portion of another absorbent article incorporating a representative fluted absorbent composite formed in accordance with the present invention.
Figure 12:
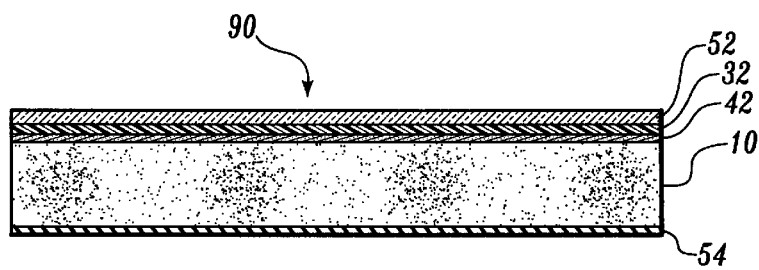
FIG. 12 is a lateral cross-sectional view of a portion of another absorbent article incorporating a representative fluted absorbent composite formed in accordance with the present invention.

A variety of suitable constructs can be produced from the absorbent composite. The most common include absorptive consumer products, such as diapers, feminine hygiene products such as feminine napkins, and adult incontinence products. For example, referring to FIG. 10, absorbent article 70 includes absorbent composite 10 and has a liquid pervious facing sheet 52 and a liquid impervious backing sheet 54. Referring to FIG. 11, absorbent article 80 includes absorbent; composite 10 and an overlying acquisition layer 32. A liquid pervious facing sheet 52 overlies acquisition layer 32, and a liquid impervious backing sheet 54 underlies absorbent composite 10. These absorbent composites will provide advantageous liquid absorption performance for use in, for example, diapers. FIG. 12 illustrates absorbent construct 90, which further includes distribution layer 42 interposed between acquisition layer 32 and composite 10.

Figure 13:
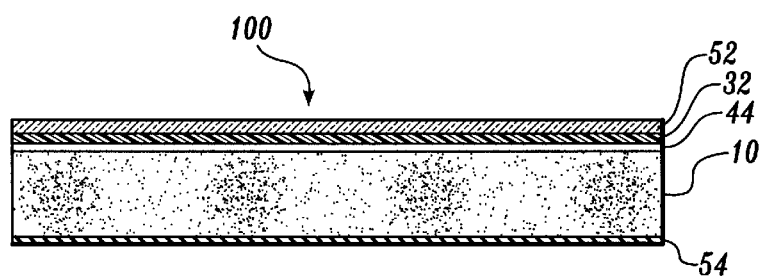
FIG. 13 is a lateral cross-sectional view of a portion of another absorbent article incorporating a representative fluted absorbent composite formed in accordance with the present invention.

One of ordinary skill will be able to make a variety of different constructs using the concepts taught herein. For example, a typical construction of an adult incontinence absorbent structure is shown in FIG. 13. Referring to FIG. 13, article 100 includes facing sheet 52, acquisition layer 32, absorbent composite 10, and backing sheet 54. Facing sheet 22 is pervious to liquid while backing sheet 24 is impervious to liquid. In this construct, a liquid pervious tissue 44 composed of a polar, fibrous material is positioned between absorbent composite 10 and acquisition layer 32.

The present invention provides a fibrous absorbent composite containing absorbent material and methods for its formation. The absorbent composite is a fibrous structure that includes absorbent material dispersed throughout the composite and in increased concentration in bands across the composite's width that extend along the composite's length. Between the bands of absorbent material, the absorbent composite includes fibrous distribution zones that prevent gel blocking in the composite. After initial liquid insult, the composite develops ridges that open the fibrous structure and increase the liquid acquisition rate for subsequent liquid insults. The combination of ridges enriched with absorbent material and fibrous distribution zones allows for total utilization of the absorbent composite as a storage core when incorporated into an absorbent article such as a diaper.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An absorbent composite, comprising a layer having
   a first region comprising absorbent material in a fibrous matrix, the first region having a first density and a first absorbent material concentration, and wherein the fibrous matrix comprises crosslinked cellulosic fibers; and
   at least one adjacent second region comprising absorbent material in a fibrous matrix, the second region having a second density and a second absorbent material concentration, wherein the second density is greater than the first density and the second absorbent material concentration is greater than the first absorbent material concentration, and wherein the fibrous matrix comprises crosslinked cellulosic fibers, and wherein the second region comprises a band along the composite's length;
   wherein the absorbent material has an absorbent capacity greater than the cellulosic fibers.

2. The composite of claim 1, wherein the at least one second region comprises a plurality of bands along the composite's length.

3. The composite of claim 2, wherein the plurality of bands are substantially parallel.

4. The composite of claim 1, wherein the at least one second region is continuous along the composite's length.

5. The composite of claim 1, wherein the at least one second region is discontinuous along the composite's length.

6. The composite of claim 1, wherein the composite is an airlaid composite.

7. The composite of claim 1, wherein the fibrous matrix comprises fluff pulp fibers.

8. The composite of claim 7, wherein the fluff pulp fibers are present in the composite in an amount from about 15 to about 85 percent by weight based on the total weight of fibers in the composite.

9. The composite of claim 1, wherein the crosslinked fibers are present in the composite in an amount from about 15 to about 85 percent by weight based on the total weight of fibers in the composite.

10. The composite of claim 1, wherein the absorbent material comprises superabsorbent material.

11. The composite of claim 10, wherein the absorbent material is present in the composite in an amount from about 10 to about 80 percent by weight based on the total weight of the composite.

12. An absorbent article comprising the composite of claim 1.

13. The composite of claim 1, wherein the absorbent material is capable of absorbing at least about 5 times its weight in water.

14. The composite of claim 1, wherein the absorbent material is capable of absorbing about 20 times its weight in water.

15. The composite of claim 1, wherein the absorbent material is capable of absorbing about 100 times its weight in water.

16. An absorbent composite, comprising a layer having
    a first region comprising superabsorbent material in a fibrous matrix, the first region having a first density and a first superabsorbent material concentration; and
    at least one adjacent second region comprising superabsorbent material in a fibrous matrix, the second region having a second density and a second superabsorbent material concentration, wherein the second density is greater than the first density and the second superabsorbent material concentration is greater than the first superabsorbent material concentration, and wherein the second region comprises a band along the composite's length.

17. An absorbent article comprising the composite of claim 16.

* * * * *